US008834479B2

(12) United States Patent
Aux Epaules et al.

(10) Patent No.: US 8,834,479 B2
(45) Date of Patent: Sep. 16, 2014

(54) PROSTHETIC ACETABULAR CUP INSERTER AND IMPACTOR

(75) Inventors: Arnaud Aux Epaules, Saint Aubin sur Mer (FR); Antoine Coustance, Hérouville St Clair (FR)

(73) Assignee: Stryker Ireland Limited (IE)

( * ) Notice: Subject to any disclaimer, the term of this patent is extended or adjusted under 35 U.S.C. 154(b) by 379 days.

(21) Appl. No.: 13/302,376

(22) Filed: Nov. 22, 2011

(65) Prior Publication Data

US 2012/0136360 A1     May 31, 2012

(30) Foreign Application Priority Data

Nov. 25, 2010  (GB) .................................. 1020041.8

(51) Int. Cl.
*A61B 17/56*    (2006.01)
*A61F 2/46*     (2006.01)
*A61F 2/30*     (2006.01)

(52) U.S. Cl.
CPC ..... *A61F 2/4609* (2013.01); *A61F 2002/30378* (2013.01); *A61F 2002/305* (2013.01); *A61F 2002/30484* (2013.01); *A61F 2002/4627* (2013.01)
USPC .......................................................... 606/91

(58) Field of Classification Search
USPC ................. 606/86 R, 88, 89, 91, 99, 100; 623/22.12
See application file for complete search history.

(56) References Cited

U.S. PATENT DOCUMENTS

| 5,169,399 | A | * | 12/1992 | Ryland et al. ................... 606/91 |
| 5,171,243 | A | | 12/1992 | Kashuba et al. |
| 5,417,696 | A | | 5/1995 | Kashuba et al. |
| 5,954,727 | A | | 9/1999 | Collazo |
| 7,341,593 | B2 | | 3/2008 | Auxepaules et al. |
| 7,462,180 | B2 | | 12/2008 | Raugel et al. |
| 7,621,921 | B2 | | 11/2009 | Parker |
| 7,833,276 | B2 | | 11/2010 | Auxepaules et al. |
| 7,993,348 | B2 | | 8/2011 | Conte et al. |
| 2004/0215200 | A1 | * | 10/2004 | Tornier et al. ................... 606/91 |
| 2006/0149285 | A1 | | 7/2006 | Burgi et al. |

(Continued)

FOREIGN PATENT DOCUMENTS

| EP | 1570815 A1 | 9/2005 |
| FR | 2701206 A1 | 8/1994 |
| FR | 2948013 A1 | 1/2011 |
| WO | 2009136284 A1 | 11/2009 |

OTHER PUBLICATIONS

Extended European Search Report for Application No. 11250902 dated Mar. 13, 2012.

*Primary Examiner* — Christopher Beccia
(74) *Attorney, Agent, or Firm* — Lerner, David, Littenberg, Krumholz & Mentlik, LLP

(57) ABSTRACT

A prosthetic acetabular cup inserter and impactor has a body, and a cup engaging element disposed at a first end of the body and adapted to engage an inner surface of a cup with which it is used via outward biasing of the cup engaging element. The cup engaging element increases in cross-sectional area from an inner end thereof to a fullest transverse section, and decreases in cross-sectional area from said fullest transverse section to an outer end thereof. The cup engaging element has a tapered central bore engaged by a conically tapered actuation element moveable in the bore. The cup engaging element has a slot therethrough allowing the element to resiliently expand on movement of the actuator in the bore.

12 Claims, 3 Drawing Sheets

(56) References Cited

U.S. PATENT DOCUMENTS

2007/0270783 A1 11/2007 Zumsteg et al.
2008/0021481 A1 1/2008 Burgi
2011/0130763 A1 6/2011 Aux Epaules et al.
2011/0184423 A1 7/2011 Rushton et al.

* cited by examiner

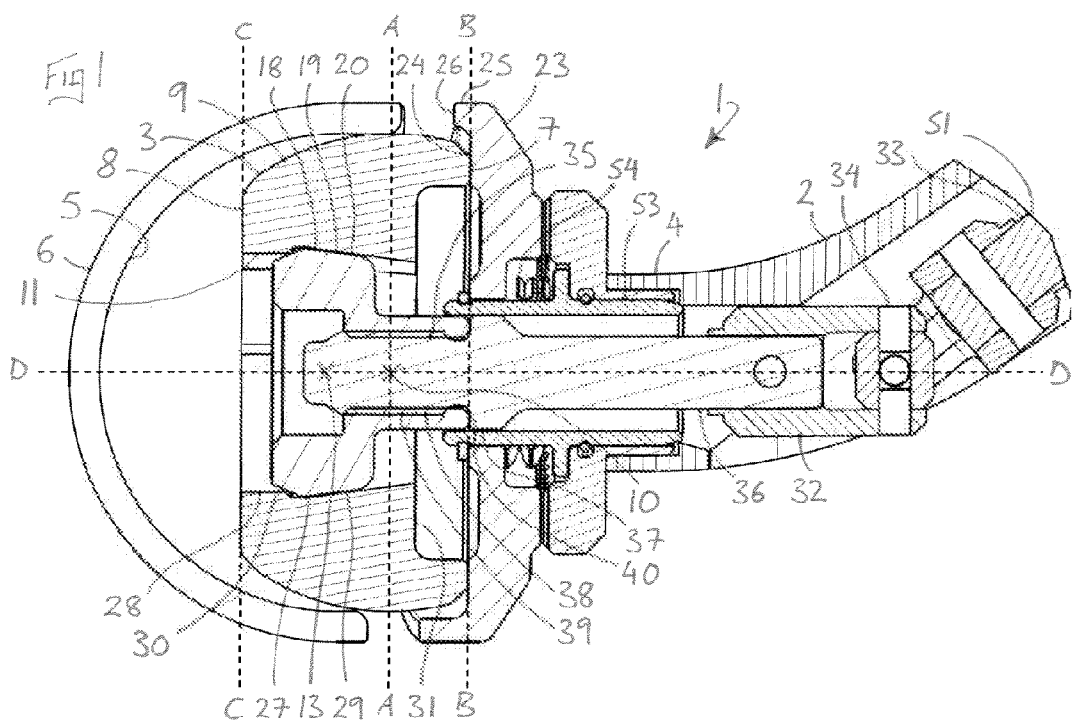
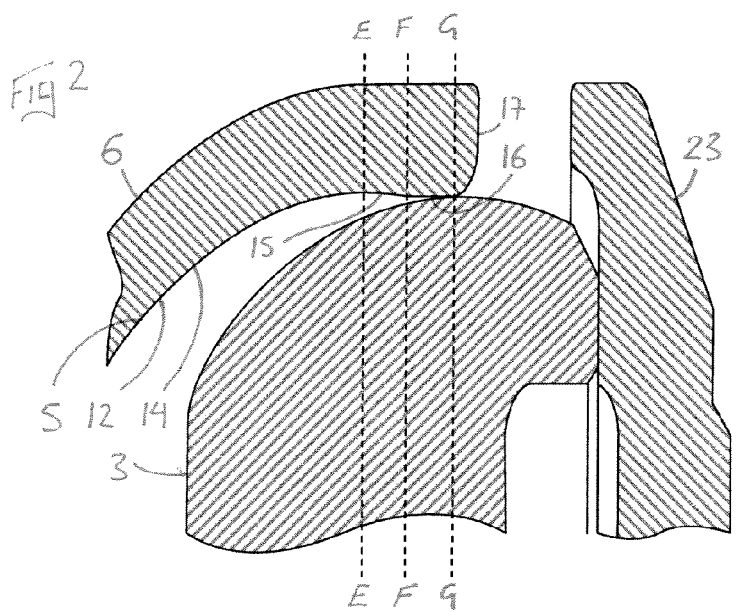

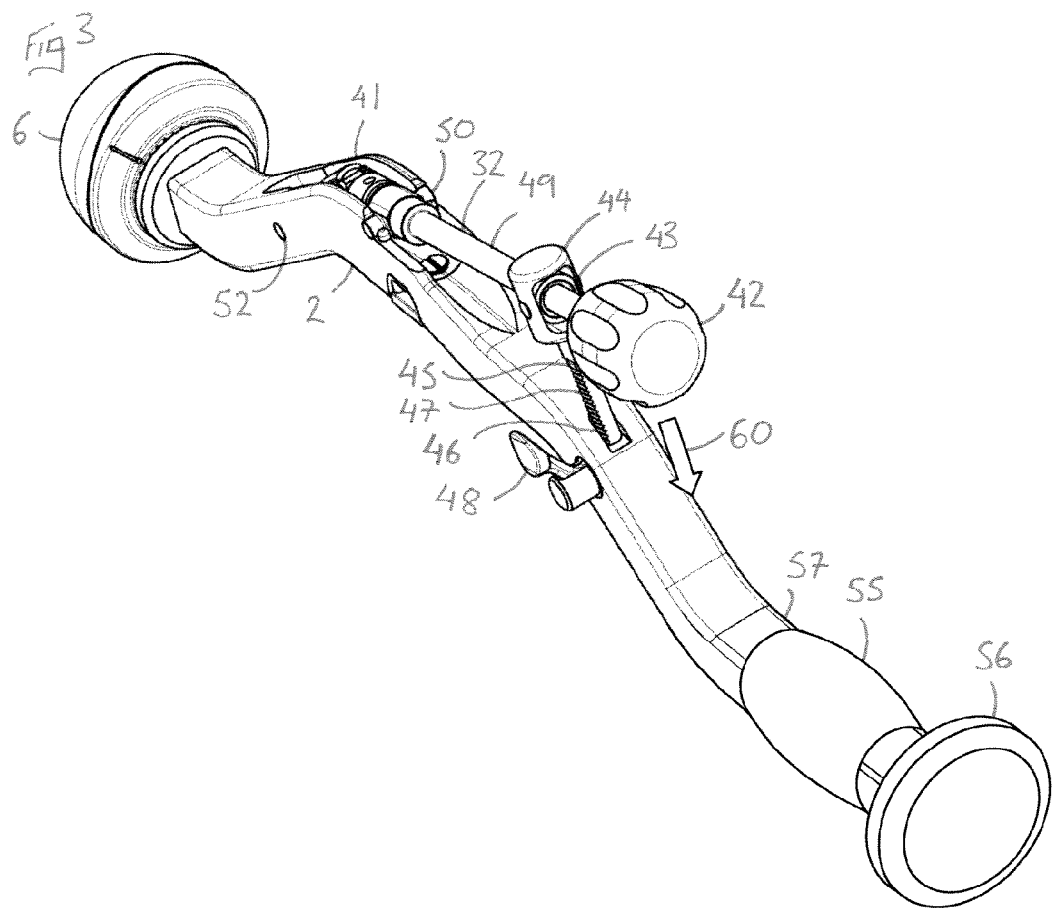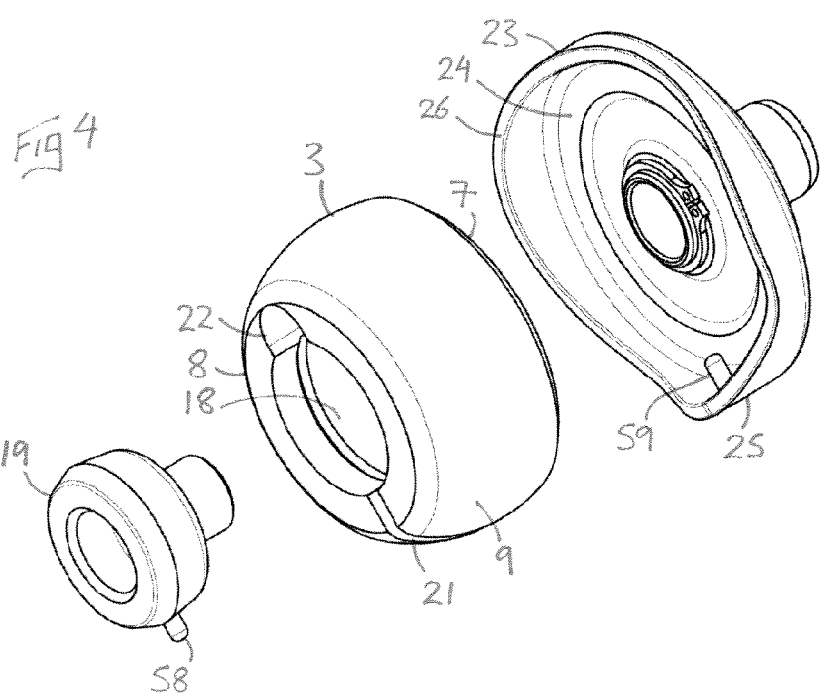

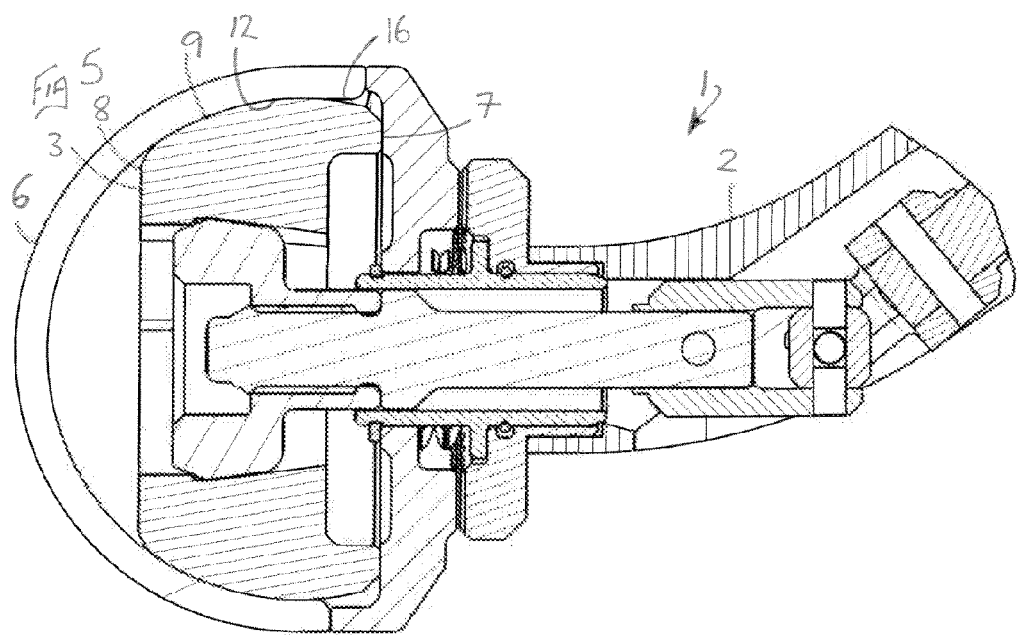
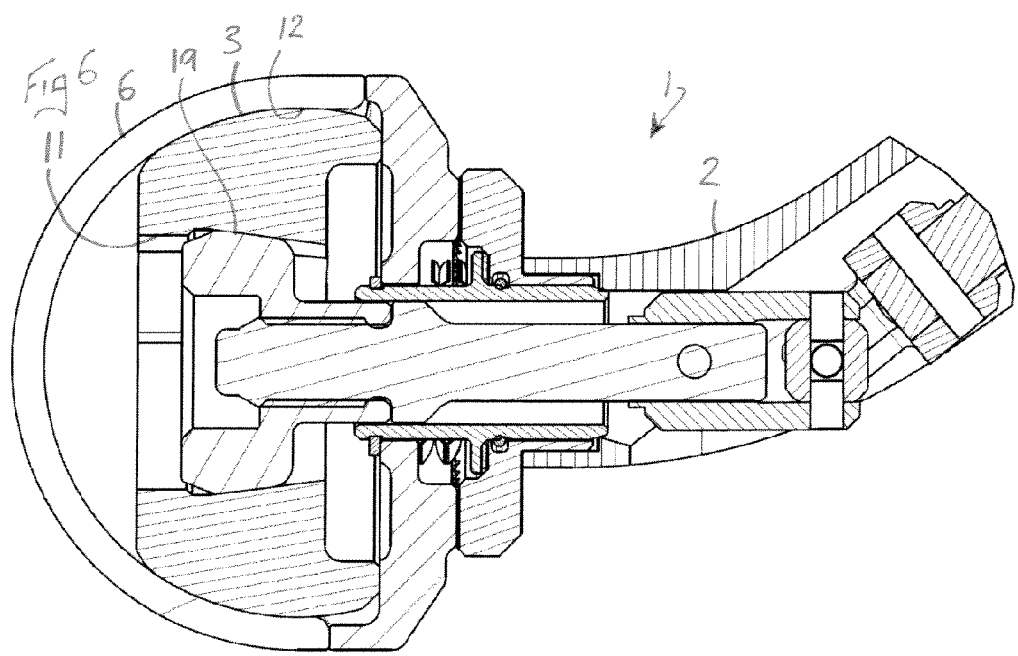

PROSTHETIC ACETABULAR CUP INSERTER AND IMPACTOR

CROSS-REFERENCE TO RELATED APPLICATION

The present application claims priority from Great Britain Patent Application No. 1020041.8 filed Nov. 25, 2010, the disclosure of which is hereby incorporated herein by reference.

BACKGROUND OF THE INVENTION

The present invention relates to a prosthetic acetabular cup inserter and impactor, for use particularly, but not exclusively, in minimal invasive surgery (MIS) with a short incision.

Prosthetic acetabular cup inserter and impactors are used to implant prosthetic acetabular cups into the cavity of a patient's hip, and generally comprise an elongate straight or curved body with a cup engaging head at a first end thereof, and a handle and impaction anvil at a second end thereof. The surgeon releasably fits a cup implant to the cup engaging head, and then positions the cup inside the patient's hip. He then applies a hammering force to the impaction anvil to secure the cup in place, before releasing the cup from the cup engaging head.

There are several known types of cup engaging head, which use different methods to releasably engage a cup. A common arrangement is to provide a screw threaded hole in the top of the cup, which can be fitted to a threaded head at a first end of the body. Such an arrangement is shown in U.S. Pat. No. 7,621,921 in the name of SYMMETRY MEDICAL, INC. In this case a threaded head is provided at a first end of a curved body, onto which is screwed a cup with a screw threaded hole. To release the cup from the inserter and impactor the threaded head is collapsed. This is necessary because the threaded head is not rotatable in relation to the body of the inserter and impactor.

U.S. Patent Application Publication No. 2008/0021481 in the name of BURGI discloses another screw thread arrangement, but this time the threaded head is disposed at the end of an axially rotatable drive train carried by the body of the inserter and impactor. Therefore, a handle at the end of the drive train is rotated to screw the threaded head into and out of the cup.

Other devices owned by the assignee of the present invention or its affiliates are U.S. Pat. Nos. 7,341,593, 7,462,180 and 7,993,348, and U.S. Patent Application Publication Nos. 2011/0130763 and 2011/0184423

However, these devices cannot function with cups which are not provided with screw threaded holes, which may be preferred for various reasons. Therefore, it is also known to releasably engage a cup using an outwardly expandable cup engaging element applied to the inner surface of the cup.

U.S. Patent Application Publication No. 2007/0270783 in the name of ZUMSTEG et al discloses a cup engaging head comprising an expandable metal ring which engages the inner surface of the cup by being forced radially outwardly by relative axial movement of a cone arranged inside it. The ring has a plurality of projections which engage corresponding radial grooves in the inner surface of the cup. This arrangement does away with the requirement for a screw threaded hole, but requires radial grooves instead, which again may not be desirable from both a performance and manufacturing point of view.

U.S. Patent Application Publication No. 2004/0215200 in the name of TORNIER et al discloses a cup engaging head comprising a radially deformable supple ring, which again engages the inner surface of the cup by being forced to expand by relative axial movement of a cone. However, this time the ring comprises a plurality of resilient petals which are simply pressed against the inner surface of the cup to engage it. This is advantageous because the inner surface of the cup can be free from any engagement formations.

In U.S. Pat. No. 7,341,593 and U.S. Patent Application Publication No. 2011/0130763, both in the name of the applicant, there are disclosed further prosthetic acetabular inserter and impactors which engage the inner surface of a cup by means of a resilient ring. In U.S. Pat. No. 7,341,593 a cylindrical flexible ring is disposed on a plate at the first end of the body, and an axial displaceable operating member with an outer rim overlying the ring is drawn towards the plate to compress the ring so it if forced radially outwardly against the inner surface of the cup. In U.S. Patent Application Publication No. 2011/0130763 a rather different configuration is disclosed, in which an expandable resilient ring is drawn back onto a static expander cone to force it to radially outwardly expand and engage the inner surface of the cup.

However, all of these resilient expandable rings suffer from a certain problem when they are used with a particular type of cup. Prosthetic acetabular cups are commonly polished to a high degree on their inner surface, and this process creates a part-spherical inner bearing surface which is slightly larger than a hemisphere. In other words, the outer rim of the cup has a smaller diameter than the largest diameter of the inner bearing surface. In most cups there is a substantially cylindrical neck portion extending from the inner bearing surface to the outer rim. This means that when resilient radially outwardly expanding rings like those described above are used to engage a cup, the ring actually engages the neck portion, and not the inner bearing surface. This is because all known rings are either cylindrical in shape, or hemi-spherical, and therefore come into contact with the neck of the cup due to its smaller diameter. This is not an issue when the neck of the cup extends far enough for a sufficient grip to be established, and this is the case with known cups with a flat outer rim.

However, U.S. Pat. No. 7,833,276, in the name of the applicant discloses a prosthetic acetabular cup comprising an inner part-spherical bearing surface and an outer peripheral rim portion which is shaped to mimic the contours of the natural shape of an acetabulum. The outer peripheral rim portion has an illium rim portion, an ischium rim portion and a pubis rim portion. The portions of the rim between the pubis rim portion and the illium rim portion and between the pubis rim portion and the ischium rim portion are concave and slightly more proximal than the pubis rim portion; the portions of the rim between the illium rim portion and the pubis rim portion, and between the illium rim portion and the ischium rim portion are more concave and proximal than the illium rim portion; and the portions of the rim between the ischium rim portion and the illium rim portion and between the ischium rim portion and the pubis rim portion are more concave and proximal than the ischium rim portion.

With this construction of cup, the neck portion is particularly short at the concave portions between the illium rim portion, the ischium rim portion and the pubis rim portion, and at the pubis rim portion itself. In fact, the neck only really has any significant extent at the illium rim portion and the ischium rim portion. The result is that when the known resilient radially outwardly expanding rings are used with these cups, engagement is only really achieved at the illium rim portion and the ischium rim portion, and this is not sufficient to properly engage the cup for insertion into the patient.

The present invention is intended to overcome some of the above problems.

BRIEF SUMMARY OF THE INVENTION

Therefore, according to the present invention, a prosthetic acetabular cup inserter and impactor comprises a body and a cup engaging element disposed at a first end of the body and adapted to engage an inner surface of a cup with which it is used via outward biasing thereof. The cup engaging element increases in cross-sectional area from an inner end thereof to a fullest transverse section, and decreases in cross-sectional area from said fullest transverse section to an outer end thereof.

Thus, the cup engaging element of the present invention has a shape which allows it to engage the inner bearing surface of a cup which is greater than hemi-spherical in shape, without any outward biasing or expansion being delimited by the narrower neck portion of the cup. It has been found that this shape of cup engaging element functions well with the type of cup disclosed in U.S. Pat. No. 7,833,766 and described above. The disclosure of U.S. Pat. No. 7,833,766 is incorporated herein by reference.

The cup engaging element can be any shape which is capable of engaging the inner surface of the cup, however preferably the cup engaging element can comprise an exterior surface which is part-spherical, and which increases in diameter from the inner end to the fullest transverse section, and decreases in diameter from the fullest transverse section to the outer end. This is the most expedient construction as it provides the greatest contact area between the cup engaging element and the inner surface of the cup.

The term "biasing" is used here because the invention includes cup engaging elements which outwardly expand to engage a cup, as well as those which fit snugly inside a cup and then engage it by being compressed into greater contact therewith, or a mixture of both.

The means by which the cup engaging element is radially outwardly biased can be any of the known arrangements described above. For example, the cup engaging element could be drawn onto a static expander in the manner disclosed in U.S. Patent Application Publication No. 2011/0130763, the disclosure of which is incorporated herein by reference. However, preferably the inserter and impactor can further comprise biasing elements adapted to bias the cup engaging element outwardly via relative axial movement therewith, and operating elements adapted to axially move the biasing means relative to the engaging element.

Such a construction could involve the outer end of the cup engaging element being acted upon in the manner disclosed in U.S. Pat. No. 7,341,593, or the cup engaging element could be forced to expand by having a cone element forced into its inner end in the manner disclosed in U.S. Patent Application Publication No. 2004/0215200. However, preferably the cup engaging element can comprise a resilient ring comprising a central aperture having an inner surface which tapers in a direction toward the first end of the body, and the biasing element can comprise a cone element disposed within the aperture and which comprises an outer surface having a taper corresponding with that of the inner surface. Therefore, axial movement of the cone element inside the resilient ring causes it to expand and engage the cup, and/or be compressed into greater contact therewith. This arrangement is neater and simpler than having an expander which overlies the resilient ring, or moving the resilient ring itself onto an expander. The operating elements can easily connect to the cone element within the resilient ring, and reverse axial movement can be readily achieved.

In one version of the invention the operating elements can axially move the cone element from a preliminary position into an engaged position, and in the engaged position the cup can be fully engaged with the cup engaging element. However, in an enhanced version of the invention in the preliminary position the cup can be partially engaged with the cup engaging element. This allows the cup to be initially held in place on the inserter and impactor, before the operating element is operated to axially move the cone element into the engaged position. In such a construction the cup engaging element is compressed into greater contact with the cup to engage it fully, rather than physically expanding outwardly, although there may be a degree of this in practice. Having partial engagement is advantageous when one hand is required to hold the body while the other is required to operate the operating elements.

This arrangement also finds particular application with prosthetic acetabular cup inserter and impactors in which the operating elements are adapted to axially rotate the cup and/or an associated impaction plate in relation to the body, because it allows the cup to be initially held in place for this process, before it is fully engaged prior to actual insertion into the patient. Such an arrangement is disclosed in the co-pending patent application entitled "Prosthetic Acetabular Cup Inserter And Impactor" filed on the same day as the present application and assigned to the assignee of the present application for a prosthetic acetabular cup inserter and impactor comprising a body, a cup engaging element disposed at a first end of the body and adapted to engage an inner surface of a cup with which it is used, and operating elements adapted to axially rotate the cup engaging element in relation to the body in use, in which an impaction plate adapted to engage a rim of said cup is disposed between the body and the cup engaging means, and in which the impaction plate is connected to the operating elements by a linkage which acts to axially rotate the impaction plate in unison with the cup engaging element in use.

The manner in which the cup engaging element of the invention is mounted to the first end of the body, and is supported for the above described radial outward biasing, can be any known practical arrangement. However, preferably a plate can be disposed between the first end of the body and the cup engaging element, which plate can comprise a front face against which the inner end of the cup engaging element can abut. The biasing means can move towards the front face when it is moved into the engaged position. Therefore, the plate holds the cup engaging element axially in position, ensuring that the axial movement of the cone in use is converted into a radial outward biasing or expansion of the ring.

The resilient ring can comprise a slot which extends axially from the outer end to the inner end, and laterally from the inner surface to the exterior surface. The resilient ring can further comprise an axially extending groove formed in the inner surface opposite to the slot. These features allow the resilient ring to be radially outwardly biased efficiently.

In one construction the plate described above can be an impaction plate having an annular cup engaging wall adapted to engage a rim of the cup. This annular cup engaging wall can comprise an irregular upper surface comprising a plurality of convex portions. Therefore, the impaction plate can be suitable for use with a cup like that disclosed in U.S. Pat. No. 7,833,276.

The operating elements of the invention can be any mechanism which can impart an axial movement to the cone element. This could be a rigid rod which is axially displaced, like that shown in U.S. Patent Application Publication No. 2011/0130763 or U.S. Pat. No. 7,621,921 (SYMMETRY MEDICAL, INC.), a rigid rod which is axially rotated to axially displace an expander means mounted on a screw thread, like that shown in U.S. Patent Application Publication No. 2004/0215200 (TORNIER), or a flexible cable which is tensioned, like that sown in U.S. Pat. No. 7,341,593 or U.S. Patent Application Publication No. 2007/0270783 ZUMSTEG.

However, in one version of the invention the operating means can comprise a rigid drive train carried by the body and comprising a connection to the biasing element at a first end thereof, and an operating knob at a second end thereof. The operating knob can be operable to axially move the biasing element from the preliminary position into the engaged position. This is the construction of operating element employed in the applicant's co-pending patent application referred to above, and is expedient because it allows for a simple lever action or the like to be converted into the required axial relative movement which radially outwardly biases or expands the cup engaging element.

The operating knob can be operable to axially move said biasing means in any know way, for example if the rigid drive train is linear in nature, it can simply be axially moved back and forth. However, as referred to below, the body is preferably curved, so the rigid drive train can follow this curved shape. Therefore, the second end of the rigid drive train can be carried on a rack, which can be disposed in a slot in the body, and be moveable therethrough both towards and away from the body. The position of the rack can be determined by a spring loaded ratchet disposed inside said body, and which can extend laterally into the slot to engage the rack. This ratchet can be movable between an engaged position and a disengaged position. In the engaged position the ratchet can allow the rack to ride over it when the rack is moved towards the body, and it can prevent the rack from moving away from the body. In the disengaged position the ratchet can allow the rack to move freely in the slot. The movement of the second end of the rigid drive train towards the body can be converted by the rigid drive train into axial movement of the biasing element into the engaged position.

In order to facilitate the above described conversion, the rigid drive train can comprise an outer end rod, an intermediary rod and an inner end rod, connected together end to end in sequence by universal joints. The outer end rod can be mounted part way along its length in a first pivot mounting, the intermediary rod can be mounted part way along its length in a second pivot mounting, and the inner rod can be mounted for axial movement in a sleeve mounted at a first end of the body. Therefore, movement of the second end of the rigid drive train towards the body can rotate the outer end rod lengthwise about the first pivot mounting in a first direction, rotate the intermediary rod lengthwise about the second pivot mounting in a second direction, and move the inner rod substantially axially through the sleeve.

It will be appreciated that the lengthwise rotation of intermediary rod may not be transmitted into a perfectly linear axial movement of inner end rod, because the universal joint therebetween follows an orbital path about the second pivot mounting. However, the required axial movement of the inner end rod is short, and any deviation caused by the orbital movement of this universal joint is well within functional tolerances.

In one construction the biasing element can be releasably fixed to the first end of the drive train with a screw thread. Alternatively, the biasing element can be releasably fixed to the first end of the drive train with a spring loaded quick release mechanism. Either of these arrangements is acceptable, but the latter allows for the inserter and impactor to be more readily dismantled.

In addition, the impaction plate can also be mounted to the first end of the body with a spring loaded quick release mechanism.

The cup engaging element can be a snap-fit onto the front face of the impaction plate. For example, it could be slightly larger than the inner diameter of the cup engaging wall, so it is retained within it. As an alternative, the cup engaging element can be disposed against the front face without constraint. This is possible because it can be held against the front face by the biasing element inside it.

A second end of the body can be provided with a handle and an impaction plate or anvil. The handle facilitates the manipulation of the inserter and impactor in use, and the impaction anvil allows for an impaction force to be imparted to the cup to fit it in the acetabulum in use.

As mentioned above, the body can be curved, in the known way which is suitable for Minimally Invasive Surgery (MIS). If this is the case, longitudinal axes of said cup engaging means and said handle can be substantially aligned. This is a known configuration, and allows the impaction force to be applied to the cup in a linear fashion.

BRIEF DESCRIPTION OF THE DRAWINGS

The present invention can be performed in various ways, but one embodiment will now be described by way of example, in which:

FIG. 1 is a cross-sectional side view of a leading portion of a prosthetic acetabular cup inserter and impactor according to the present invention, in a first in use configuration;

FIG. 2 is a partial cross-sectional side view of a portion of the prosthetic acetabular cup inserter and impactor as shown in FIG. 1, in which the image has been compressed to half its original width for illustrative purposes;

FIG. 3 is a perspective view of the prosthetic acetabular cup inserter and impactor including the leading portion as shown in FIG. 1, in a second in use configuration;

FIG. 4 is an exploded perspective view of components of the prosthetic acetabular inserter and impactor as shown in FIG. 1;

FIG. 5 is a cross-sectional side view of the portion of the prosthetic acetabular inserter and impactor as shown in FIG. 1, in said second in use configuration; and FIG. 6 is a cross-sectional side view of the portion of the prosthetic acetabular inserter and impactor as shown in FIG. 1, in a third in use configuration.

DETAILED DESCRIPTION

As shown in FIG. 1, a prosthetic acetabular cup inserter and impactor 1 comprises a body 2 and a cup engaging element 3 disposed at a first end 4 of body 2 and adapted to engage an inner surface 5 of a cup 6 with which it is used via an outward biasing thereof. The cup engaging element 3 increases in cross-sectional area from an inner end 7 thereof to a fullest transverse section, indicated by dashed line A-A, and decreases in cross-sectional area from said fullest transverse section A-A to an outer end 8 thereof.

The acetabular cup inserter and impactor 1 shown in the figures is the same as that in the applicant's co-pending patent application referred to above, and it comprises several special features which are not relevant to the present invention, for example an axially rotating impaction plate, springs, locking teeth and so on. The present invention relates to the particular shape and operating principals of the cup engaging element 3, and it will be appreciated that these could be applied to an acetabular cup inserter and impactor which does not include the above described special features.

Referring to the cup engaging element 3, it is a resilient ring made from a suitable material, for example rubber or a plastics material, and it comprises an exterior surface 9 which is part-spherical. In particular, the exterior surface 9 has the characteristic of being spherical because all parts of the surface 9 lie at substantially the same radius from a center point 10. However, as is clear from the figures, the sphere is truncated by being delimited by two parallel planes, indicated in FIG. 1 by lines B-B and C-C.

The ring 3 comprises a central aperture 11 aligned on an axis D-D, which is normal to parallel planes B-B and C-C. Taking the direction of D-D as a reference, the outer surface 9 of the ring 3 increases in diameter from inner end 7, at plane B-B, to a fullest transverse section at plane A-A, and decreases in diameter from fullest transverse section A-A to outer end 8, at plane C-C.

This basic structure is an essential feature of the present invention, and is designed to function with acetabular cups comprising particular characteristics, which are illustrated by FIG. 2. FIG. 2 shows an enlarged section of FIG. 1, and is shown in partial section of its original width in order to better illustrate the characteristics of the inner surface 5 of the cup 6.

In particular, the inner surface 5 of the cup 6 comprises a part-spherical inner bearing surface 12. The inner bearing surface 12 has the characteristic of being spherical because all parts of it lie at the same radius from a center point 13 (shown in FIG. 1). As is clear from FIG. 2, with the cup 6 axially aligned on axis D-D, the inner bearing surface 12 is slightly larger than a hemisphere. In particular, it comprises a hemispherical portion 14 which extends to plane E-E, and an additional portion 15 which extends to plane F-F. This greater than hemispherical shape is created during manufacture when inner bearing surface 12 of the cup 6 is polished.

The cup 6 also comprises a neck portion 16, which is cylindrical and extends from plane F-F to plane G-G. Therefore, outer rim 17 of cup 6 has a smaller diameter than the largest diameter of inner bearing surface 12, at plane E-E.

The outer rim 17 of cup 6 is shaped to mimic the contours of the natural shape of an acetabulum, and is the same as that disclosed in U.S. Pat. No. 7,833,276. As referred to above, with this construction of cup neck portion 16 is particularly short at the concave portions between the illium rim portion, the ischium rim portion and the pubis rim portion, and at the pubis rim portion itself. In fact, neck 16 only really has any significant extent at the illium rim portion and the ischium rim portion.

Referring to FIG. 1, the central aperture 11 has an inner surface 18 which tapers in a direction toward the first end 4 of the body 2. Disposed inside the aperture 11 is a biasing element in the form of cone element 19, which has an outer surface 20 having a taper corresponding with that of inner surface 18. Therefore, relative axial movement of the cone element 19 towards the first end 4 of the body 2 in use causes the ring 3 to be radially outwardly biased and/or expanded to engage the cup 6.

Referring to FIG. 4, the ring 3 comprises a slot 21 which extends axially from outer end 8 to inner end 7, and laterally from inner surface 18 to exterior surface 9. The ring further comprises an axially extending groove 22 formed in inner surface 18 opposite to slot 21. The groove 22 also extends from outer end 8 to inner end 7. These features allow the ring 3 to be radially outwardly biased and/or expanded efficiently in use.

Referring back to FIG. 1, an impaction plate 23 is disposed between the body 2 and the ring 3. The impaction plate 23 has a front face 24 against which the inner end 7 of the ring 3 abuts. Cone 19 moves towards front face 24 when it is moved into the engaged position, and impaction plate 23 holds ring 3 axially in position when this happens, as described further below, ensuring that the axial movement of cone 19 is converted into a radial outward biasing and/or expansion of ring 3.

The impaction plate 23 also has annular cup engaging wall 25, which has an irregular upper surface 26 adapted to engage outer rim 17 of cup 6.

The central aperture 11 comprises a first portion 27 which comprises the above described taper, and a second narrower portion 28 above first portion 27. The cone element 19 comprises a first portion 29 which comprises the above described taper, and a second portion 30 above first portion 29, which tapers in the opposite direction. The second portion 28 of aperture 11 serves to retain cone element 19 therein. It may also prevent ring 3 from moving axially towards the front face 24 of the impaction plate 23 when the cup 6 is initially applied to the ring 4 in use, as described further below. The second portion 28 of the aperture 11 engages the second portion 30 of the cone element 19, and significant axial compression of the resilient ring 3 is prevented. The second portion 28 of the aperture 11 also assists in the dismantling of the cone element 19 and the ring 3. When the cone element 19 is removed from the aperture 11, the second portion 30 of the cone element 19 engages the second portion 28 of the aperture 11 and forces the resilient ring 3 to expand, allowing the cone 19 to be freed.

The resilient ring 3 also comprises a recess 31 formed in the inner end 7, which provides space for other components.

The prosthetic acetabular cup inserter and impactor 1 also comprises operating elements, in the form of rigid drive train 32, which is adapted to axially move the cone 19 relative to the ring 3. The drive train 32 is carried by the body 2, and comprises a number of rods 33, held together with universal joints 34. As is clear from FIG. 3, the body 2 is curved, in the known way which is suitable for MIS, and the drive train 32 is adapted to follow this curved shape.

The cone 19 is connected to a first end 35 of the drive train 32. An inner end rod 36 comprises a collar 37 and a screw threaded portion 38. The cone 19 comprises a corresponding central aperture 39 provided with a screw thread, which is screwed onto to screw threaded portion 38, such that an underside 40 of the cone 19 abuts against collar 37.

Referring to FIG. 3, the drive train 32 emerges from the body 2 at an intermediary opening 41. An operating knob 42 is provided at a second end 43 of the drive train 32. Movement of the operating knob 42 towards the body 2 moves the cone 19 from a preliminary position into an engaged position, as described further below. (Axial rotation of the operating knob 42 is transmitted into axial rotation of the cone element 4 via axial rotation of the rods 33 and universal joints 34 of the drive train 32. However, this functionality is not of relevance to the present invention, so is not further described here in any detail.)

The second end 43 of the drive train 32 is supported by an adjustable housing 44, mounted on the end of a rack 45. The rack 45 is disposed in a slot 46 in the body 2, and is moveable therethrough both towards and away from the body 2. The position of the rack 45 is determined by a spring loaded ratchet (not visible) which is disposed inside the body 2, and which extends laterally into slot 46 to engage the toothed surface 47 of the rack 45 and hold it in position. In an engaged position the ratchet is configured to allow the rack 45 to ride over it when it is moved towards the body 2, but to prevent the rack 45 from moving away from the body 2. In a disengaged position the ratchet allows the rack 45 to move freely in the slot 46. Engagement and disengagement of the ratchet is controlled by lever 48. In the position shown in FIG. 3 the ratchet is in the engaged position, and movement of the lever 48 away from the body 2 disengages the ratchet.

Movement of the rack 45 and the housing 44 towards the body 2 rotates outer end rod 49 lengthwise about first pivot mounting 50. Outer end rod 49 is connected to intermediary rod (visible in FIG. 1) beyond the first pivot mounting 50, and therefore lengthwise rotation of the outer end rod 49 about first pivot mounting 50 rotates intermediary rod 51 lengthwise about its own second pivot mounting 52. Intermediary rod 51 is connected to inner end rod 36 (again visible in FIG. 1) beyond second pivot mounting 52, and therefore lengthwise rotation of the intermediary rod 51 about pivot mounting 52 axially moves the inner end rod 36 through a sleeve 53 mounted between the body 2 and the inner end rod 36. This draws the cone 19 towards the impaction plate 23, which serves to outwardly bias and/or expand the ring 3 to engage the cup 6.

Movement of the rack 45 and the housing 44 away from the body 2 achieves the opposite result. Although in fact, when the ratchet is disengaged the ring 3 is released from its outwardly biased state, and it contracts back to its neutral state, pushing the cone 19 back out, which in turn acts to move the drive train 32 in the opposite manner to as described above, forcing the rack 45, housing 44 and operating knob 22 to move away from the body 2. (When the rack 45 is disengaged like this a spring 54 mounted between the body 2 and the impaction plate 23 acts to axially move the impaction plate 23 on the sleeve 53. However, this axial movement of the impaction plate 23 is once again functionally not of relevance to the present invention, so it is not further described here in any detail.)

It will be appreciated that the lengthwise rotation of intermediary rod 51 is not transmitted into a perfectly linear axial movement of inner end rod 36, because the universal joint 34 therebetween follows an orbital path about pivot mounting 52. However, the required axial movement of the inner end rod 36 is short, and any deviation caused by the orbital movement of the universal joint 34 is well within functional tolerances.

The body 2 had a handle 55 and an impaction anvil 56 at a second end 57 thereof. The handle 55 facilitates the manipulation of the body 2 in use, and the impaction anvil 56 allows for an impaction force to be imparted to the cup 6 to fit it in the acetabulum in use. The longitudinal axes of the ring 3 and handle 55 are aligned so the impaction force is applied to the cup 6 in a linear fashion. Such a configuration is known, and is not further described here.

Referring to FIG. 4, cone 19 has a radially outwardly extending spigot 58, and the impaction plate 23 has a radially inwardly extending spigot 59 provided on the cup engaging wall 25, both of which fit into the slot 21. These features facilitate the transmission of axial rotation of the cone 19 to the impaction plate 23, which once again is a feature which is not relevant to the present invention, so is not further described here in any detail.

In use the inserter and impactor 1 operates as follows. Prior to engagement with the cup 6, the cone element 19 is arranged in the preliminary position. This is achieved by placing the ratchet in its disengaged position, so the ring 3 is not outwardly biased or expanded and holds the cone element 19 at an outer end of the first portion 27 of the central aperture 11. The ratchet is then engaged by movement of the lever 48 towards the body 2, so that the operating knob 42 will be held in position when later moved towards the body 2 as described below.

As shown in FIG. 1, the surgeon then introduces a cup 6 to the ring 3. With the cone 19 in the preliminary position as shown, the cup 6 can be forced onto the ring 3 and held in place as shown in FIG. 5. As such, the cup 6 is partially engaged on the ring 3, as it can be manually removed fairly easily if required. During this mounting process the second portion 28 of the aperture 11 may engage the second portion 30 of the cone 19 to prevent significant axial compression of the resilient ring 3.

It will be appreciated from FIG. 5 that because the exterior surface 9 of the ring 3 increases in cross-sectional area from the inner end 7 to a fullest transverse section at plane A-A, and then decreases in cross-sectional area to the outer end 8, once the fullest transverse section of the ring 3 has passed through the neck portion 16 of the cup 6, that section expands and engages the inner bearing surface 12 of the cup 6. As is clear from FIG. 5, the exterior surface 9 ring 3 is specifically shaped to mirror the inner bearing surface 12, so contact is made across most of the exterior surface 9 of the ring 3. This provides a far larger contact area than would be achieved with a known conical or cylindrical ring, which would only engage the neck portion 16 of the cup 6.

Referring to FIGS. 1 and 2, it should be noted that a portion of the ring 3 between the fullest transverse section at plane A-A and the inner end 7 engages the additional portion 15 of the inner bearing surface 12 between planes E-E and F-F. Not only does this increase the contact made between these surfaces, it also acts to hold the cup 6 in place on the ring 3, in the manner of a snap-fit, because the fullest transverse section of the ring 3 at plane A-A is wider than the neck portion 16 of the cup 6.

The cup 6 is aligned with the cup engaging wall 25 such that the irregular shapes of the upper surface 26 of the wall 25 and the rim 17 of the cup 6 fit together.

At this point the surgeon can axially rotate the knob to align the cup 6 and impaction plate 23 as desired in relation to the body 2. However, as mentioned above, this functionality is not relevant to the present invention, so is not further described here in any detail.

Once the cup 6 is in place as shown in FIG. 5, the surgeon then pushes the operating knob 42 downward towards the body 2, as indicated by arrow 60 in FIG. 3, rotating the outer end rod 49 lengthwise in a clockwise direction about the first pivot mounting 50. As described above, this lengthwise rotational movement of the outer end rod 49 is transmitted to the cone element 19 via the lengthwise rotational movement of the intermediary rod 51 and the axial movement of the inner end rod 32, so the cone element 19 is axially moved a short distance towards the impaction plate 23, to the position illustrated in FIG. 6. (In practice the impaction plate 23 initially moves axially on sleeve 53 from the position shown in FIG. 5 until it abuts against a collar component 55, against the force of spring 54, as illustrated in FIG. 6. However, again this feature is not relevant to the present invention.)

In this engaged position the ring 3 is radially outwardly biased, and is forced into greater contact with the inner bearing surface 12 of the cup 6, by virtue of the relative movement of the tapered cone 19 inside the tapered central aperture 11. This radial biasing compresses the ring 3 against the inner bearing surface 12 of the cup 6, firmly fixing the cup in a fully engaged position. In contrast to the partially engaged position shown in FIG. 5, the cup 6 cannot be readily manually removed from the ring 3.

Downward movement of the operating knob 42 towards the body 2 forces the rack 45 to ride over the ratchet until the engaged position is achieved, and then the ratchet locks the cone 19 in position.

Now the cup 6 is fully engaged, the surgeon can introduce the inserter and impactor 1 into the patient and place the cup 6 in the acetabulum. They can then use a hammer or similar tool to impart an impaction force to the anvil 56 at the second end 57 of the body 2, which acts to firmly locate the cup 6 in the acetabulum.

To release the cup 6 from the inserter and impactor 1 the lever 48 is moved away from the body 2 so the rack 45 is disengaged. The ring 3 is then released from its outwardly biased state, contracts and returns to the cone 19 to the preliminary position. In this state the ring 3 can be readily manually removed from the cup 7.

After surgery the inserter and impactor 1 can be dismantled for cleaning. The ring 3 can be pulled from the cone by virtue of its resilience. The cone 19 can then be unscrewed from the inner end rod 32 and removed therefrom.

The above described embodiment can be altered without departing from the scope of the claims. For example, in other alternative embodiments (not shown) inserter and impactors are provided which do not include the additional features forming a part of inserter and impactor 1 which are not relevant to the present invention. In particular, in one alternative embodiment (not shown), the impaction plate is statically mounted to the first end of the body, and the rigid drive train does not axially rotate the cone, the ring or the impaction plate in relation to the body. In another alternative embodiment (not shown) the body is straight, and the operating means is a straight rod which is axially moved in the body to actuate the cone. In other alternative embodiments (not shown), the body is either straight or curved, and the operating means is a flexible, tensionable cable.

In other alternative embodiments (not shown) other types of biasing means are employed to outwardly bias the ring. For example, in one alternative embodiment (not shown) the resilient ring is drawn onto a static expander in a manner like that disclosed in U.S. Patent Application Publication No. 2011/0130763. In another alternative embodiment (not shown) the outer end of the ring is depressed by an overlying expander means in a manner like that disclosed in U.S. Pat. No. 7,341,593. In another alternative embodiment (not shown) the ring is forced to expand by having a cone forced into its inner end in a manner like that disclosed in U.S. Patent Application Publication No. 2004/0215200.

In another alternative embodiment (not shown), the resilient ring is a snap-fit onto the front face of the impaction plate. The ring can be slightly larger than the inner diameter of the cup engaging wall, so it is retained within it.

In another alternative embodiment (not shown) the cone is releasably fixed to the first end of the drive train with a spring loaded quick release mechanism. This allows for the inserter and impactor to be more readily dismantled.

Thus, the present invention provides a cup engaging ring with a shape which allows it to properly and effectively engage a cup with an inner bearing surface which is greater than hemi-spherical in shape and with a neck portion of very limited extent.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A prosthetic acetabular cup inserter and impactor comprising a body, and a cup engaging element disposed at a first end of said body and adapted to engage an inner surface of a cup with which it is used via outward biasing thereof, in which said cup engaging element increases in cross-sectional area from an inner end thereof to a fullest transverse section, and decreases in cross-sectional area from said fullest transverse section to an outer end thereof;

wherein said cup engaging element comprises an exterior surface which is part-spherical, and which increases in diameter from said inner end to said fullest transverse section, and decreases in diameter from said fullest transverse section to said outer end;

and further comprising biasing means adapted to bias said cup engaging element outwardly via relative axial movement therewith, and operating means adapted to axially move said biasing means relative to said cup engaging element in which said cup engaging element comprises a resilient ring comprising a central aperture having an inner surface which tapers in a direction toward said first end of said body, and in which said biasing means comprises a cone element disposed within said aperture and which comprises an outer surface having a taper corresponding with that of said inner surface;

wherein said operating means axially moves said cone element from a preliminary position into an engaged position, in which in said engaged position said cup is fully engaged with said cup engaging element in which in said preliminary position said cup is partially engaged with said cup engaging element;

wherein a plate is disposed between said first end of said body and said cup engaging element, in which said plate comprises a front face against which said inner end of said cup engaging element abuts, and in which said biasing means moves towards said front face when it is moved into said engaged position; and wherein said plate comprises an impaction plate having an annular cup engaging wall adapted to engage a rim of said cup.

2. The prosthetic acetabular cup inserter and impactor as claimed in claim 1 in which said resilient ring comprises a slot which extends axially from said outer end to said inner end, and laterally from said inner surface of said exterior surface.

3. The prosthetic acetabular cup inserter and impactor as claimed in claim 2 in which said resilient ring further comprises an axially extending groove formed in said inner surface opposite to said slot.

4. The prosthetic acetabular cup inserter and impactor as claimed in claim 1 in which said annular cup engaging wall comprises an irregular upper surface comprising a plurality of convex portions.

5. A prosthetic acetabular cup inserter and impactor comprising a body, and a cup engaging element disposed at a first end of said body and adapted to engage an inner surface of a cup with which it is used via outward biasing thereof, in which said cup engaging element increases in cross-sectional area from an inner end thereof to a fullest transverse section, and decreases in cross-sectional area from said fullest transverse section to an outer end thereof;

wherein said cup engaging element comprises an exterior surface which is part-spherical, and which increases in diameter from said inner end to said fullest transverse section, and decreases in diameter from said fullest transverse section to said outer end;

and further comprising biasing means adapted to bias said cup engaging element outwardly via relative axial movement therewith, and operating means adapted to axially move said biasing means relative to said cup engaging element;

wherein said cup engaging element comprises a resilient ring comprising a central aperture having an inner surface which tapers in a direction toward said first end of said body, and in which said biasing means comprises a cone element disposed within said aperture and which comprises an outer surface having a taper corresponding with that of said inner surface;

wherein said operating means axially moves said cone element from a preliminary position into an engaged position, in which in said engaged position said cup is fully engaged with said cup engaging element;

wherein which said operating means comprises a rigid drive train carried by said body and comprising a connection to said biasing means at a first end thereof, and an operating knob at a second end thereof, which operating knob is operable to axially move said biasing means from said preliminary position into said engaged position; and wherein said second end of said rigid drive train is carried on a rack, in which said rack is disposed in a slot in said body, and is moveable therethrough both towards and away from said body, in which the position of said rack is determined by a spring loaded ratchet disposed inside said body, and which extends laterally into said slot to engage said rack, in which said ratchet is movable between an engaged position and a disengaged position, in which in said engaged position said ratchet allows said rack to ride over it when said rack is moved towards said body and prevents said rack from moving away from said body, in which in said disengaged position said ratchet allows said rack to move freely in said slot, in which movement of said second end of said rigid drive train towards said body is converted by the rigid drive train into axial movement of said biasing means into said engaged position.

6. The prosthetic acetabular cup inserter and impactor as claimed in claim 5 in which said body is curved and in which said rigid drive train comprises an outer end rod, an intermediary rod and an inner end rod, connected together end to end in sequence by universal joints, in which said outer end rod is mounted part way along its length in a first pivot mounting, in which said intermediary rod is mounted part way along its length in a second pivot mounting, in which said inner rod is mounted for axial movement in a sleeve mounted at a first end of said body, in which movement of said second end of said rigid drive train towards said body rotates said outer end rod lengthwise about said first pivot mounting in a first direction, which rotates said intermediary rod lengthwise about said second pivot mounting in a second direction, which moves said inner rod substantially axially through said sleeve.

7. The prosthetic acetabular cup inserter and impactor as claimed in claim 5 in which said biasing means is releasably fixed to said first end of said drive train with a screw thread.

8. The prosthetic acetabular cup inserter and impactor as claimed in claim 5 in which said biasing means is releasably fixed to said first end of said drive train with a spring loaded quick release mechanism.

9. The prosthetic acetabular cup inserter and impactor as claimed in claim 1 in which said impaction plate is mounted to said first end of said body with a spring loaded quick release mechanism.

10. The prosthetic acetabular cup inserter and impactor as claimed in claim 1 in which said cup engaging element is a snap-fit onto said front face.

11. The prosthetic acetabular cup inserter and impactor as claimed in claim 1 in which a second end of said body is provided with a handle and an impaction anvil or plate.

12. The prosthetic acetabular cup inserter and impactor as claimed in claim 11 in which said body is curved, and in which longitudinal axes of said cup engaging means and said handle are substantially aligned.

* * * * *